United States Patent [19]

Lindemans

[11] 4,310,000
[45] Jan. 12, 1982

[54] IMPLANTABLE PULSE GENERATOR HAVING SEPARATE PASSIVE SENSING REFERENCE ELECTRODE

[75] Inventor: Fredric W. Lindemans, Kerkrade, Netherlands

[73] Assignee: Medtronic, Inc., Minneapolis, Minn.

[21] Appl. No.: 114,767

[22] Filed: Jan. 23, 1980

[51] Int. Cl.$^3$ .............................................. A61N 1/36
[52] U.S. Cl. ........................................... 128/419 PG
[58] Field of Search ...................... 128/419 P, 419 PG

[56] References Cited

U.S. PATENT DOCUMENTS

| 3,421,512 | 1/1969 | Frasier | 128/419 PG |
| 3,478,476 | 11/1969 | Greatbatch | 128/419 PG |
| 3,920,024 | 11/1975 | Bowers | 128/419 PG |
| 4,091,818 | 5/1978 | Brownlee et al. | 128/419 PG |

Primary Examiner—William E. Kamm
Attorney, Agent, or Firm—John L. Rooney; Joseph F. Breimayer

[57] ABSTRACT

Passive sensing reference electrode positioned on an implantable pulse generator where the electrode electrically contacts with tissue or body fluid. The electrode configuration reduces stimulation afterpotentials due to electrode polarization and output capacitor recharge by using the passive sensing reference electrode for sensing. The passive sensing reference electrode may be located adjacent the conductor sleeve, on a surface of a hermetically sealed metallic pacemaker can, or one of the surfaces of the pacemaker can may be insulated from another surface of the pacemaker can where one half of the pacemaker can may be the passive sensing reference electrode.

6 Claims, 7 Drawing Figures

IMPLANTABLE PULSE GENERATOR HAVING SEPARATE PASSIVE SENSING REFERENCE ELECTRODE

BACKGROUND OF THE INVENTION

1. Field of the Invention

The present invention relates generally to a surgical instrument, more particularly, pertains to a passive sensing reference electrode for an implantable pulse generator.

2. Description of the Prior Art

The delivery of an electrical stimulus to tissue induces a field which is generally orders of magnitude higher in amplitude than the field caused by the electrical activity of the tissue itself. When the stimulus ends, electrical fields remain in tissue due to two factors, the first being that electrochemical equilibrium at the electrode tissue interfaces which has been disturbed by the stimulus has to reestablish itself, and the second being that an output capacitor of the implantable pulse generator generally recharges through the same electrical circuits including the heart as through which it discharges.

When one wants to measure or sense the electrical activity of the tissue, it is generally necessary to supress or blank the sensing amplifier of the implantable pulse generator during a stimulus to avoid overloading. When the blanking is over and the sensing amplifier is reconnected to a lead connected to the implantable pulse generator forming a pacemaker, the sensing amplifier abruptly senses a different potential than was present at the time of initial blanking due to the electrode reaction and the recharging of the output capacitor which causes unwanted artifacts in the sensing signal.

FIG. 1 illustrates an electrical circuit schematic diagram of the prior art circuits showing the sense amplifier connected directly to the electrode and housing in a unipolar application, or directly to the electrodes in a bipolar application. As a consequence, when the stimulus ends, electrical fields remain in the tissue and are subsequently sensed by the sense amplifier as discussed. While the amplifier is usually suppressed or blanked during the stimulus to avoid overloading, the sensing amplifier senses a different potential than was present at the time of initial blanking when reconnected to the signal causing unwanted artifacts in the sensed signals.

The passive sensing reference electrode of the present invention provides an electrode which is positioned on the implantable pulse generator in such a way that electrical continuity with the tissue or body fluid is assured. This electrode is to be used as a reference electrode for sensing purposes only in contrast to the present situation where the surface of the pacemaker can of a unipolar implanted pulse generator or the electrode ring for a bipolar system serves as a reference or indifferent electrode for applying the stimulus current also. Ideally, a reference electrode for sensing purposes should never carry any current, as this leads to polarization and electrochemical instability at the site of the reference electrode. The proposed passive sensing reference electrode is such a reference for sensing only and its application allows for substantially shorter blanking time while avoiding the risk of improper sensing of stimulus afterpotentials.

SUMMARY OF THE INVENTION

The present invention provides a passive sensing reference electrode for an implantable pulse generator which assures electrical continuity with the tissue or tissue fluid of the body.

According to one embodiment of the present invention, there is provided in combination an implantable pulse generator including a pacemaker metallic can member and at least one output connector projecting from the can member, and a reference electrode positioned on and insulated from the pacemaker metallic can member whereby the reference electrode assures electrical continuity with the tissue or tissue fluid thereby reducing the influence of stimulation afterpotentials due to electrode polarization and output capacitor recharge of the implantable pulse generator. The passive sensing reference electrode can be positioned on a connector sleeve of the pacemaker can, on a member between the pacemaker can and the connector sleeve, insulated from a portion of the metallic surface of the pacemaker can or one half of the pacemaker can may be insulated from the other half thereby providing the passive sensing reference electrode.

A significant aspect and feature of the present invention is a passive sensing reference electrode positioned on and insulated from an implantable pulse generator metallic can which reduces the sensing of stimulation afterpotentials due to electrode polarization and output capacitor recharge.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the FIGURES thereof and wherein.

DESCRIPTION OF THE PREFERRED EMBODIMENT

Figure 3:
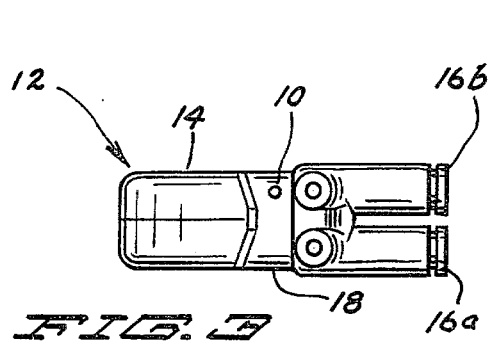
FIG. 3 illustrates a top view of FIG. 2.
Figure 1:
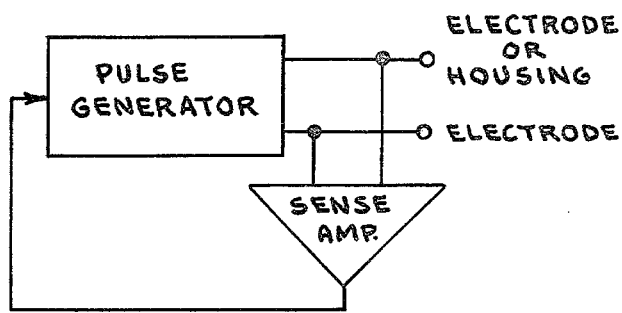
FIG. 1 illustrates an electrical circuit schematic diagram of the prior art circuits.
Figure 2:
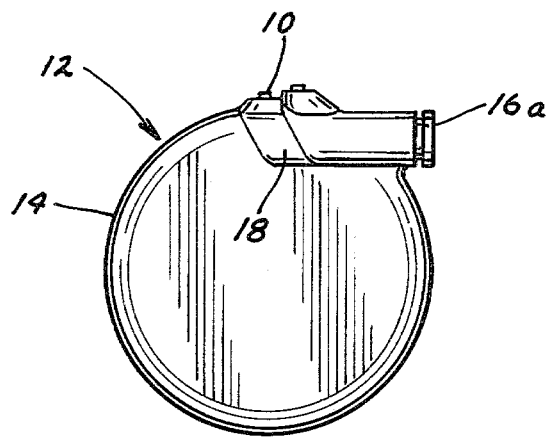
FIG. 2 illustrates a plan view of a passive sensing reference electrode, the present invention, on an implantable pulse generator metallic can.

FIG. 2, which illustrates a plan view of a passive sensing reference electrode 10 of the present invention, shows an implantable pulse generator 12 including an implantable pulse generator hermetically sealed metallic can 14 of titanium or other similar, like metal, connector sleeves 16a and 16b of silicone rubber or like material, and an insulation block 18 between the connector sleeves 16a and 16b as also illustrated in FIG. 3 and the can 14. The passive sensing reference electrode 10 of the present invention affixes to an insulation block 18. The connector sleeves 16a and 16b engage over the insulation block 18. The metallic can 14 is preferably a hermetically sealed metallic container that contains the pulse generator circuitry and power source. The passive sensing reference electrode 10 connects to an input terminal of the sense amplifier through a feedthrough not illustrated in the figure for purposes of clarity and as later described in detail.

FIG. 3, which illustrates a top view of FIG. 2, shows numerals which correspond to those elements previously delineated for FIG. 2.

Figure 4:
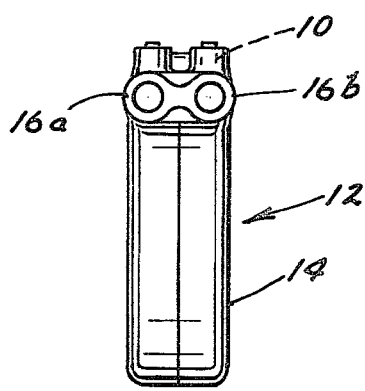
FIG. 4 illustrates an end view of FIG. 2.

FIG. 4, which illustrates an end view of FIG. 2, shows numerals which correspond to those elements previously delineated for FIG. 2.

Figure 5:
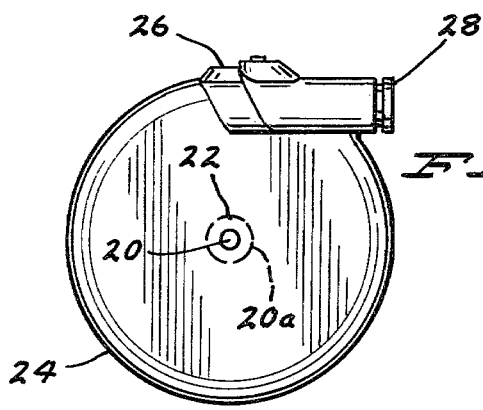
FIG. 5 illustrates a second embodiment of the present invention.

FIG. 5, which shows a second embodiment of the present invention, shows a passive sensing reference electrode 20 positioned on a midportion 22 of a hermetically sealed implantable pulse generator metallic can 24 and insulated therefrom with insulation 20a. The exact position of the passive sensing reference electrode 20 is not critical and the passive sensing reference electrode 20 can be located anywhere on the metallic can 24 as predetermined. By way of example and for purposes of illustration, the passive sensing reference electrode has been located in the midcenter 22 of the can 24, but may be located anywhere on the surface as so predetermined. A feedthrough not illustrated in the figure for purposes of clarity connects the passive sensing reference electrode 20 to an input terminal of a sense amplifier as later described. An insulator block 26 positions over a portion of the metallic can 24 and a silicone rubber connector sleeve 28 protects the connectors as previously described for FIGS. 2-4.

Figure 6:
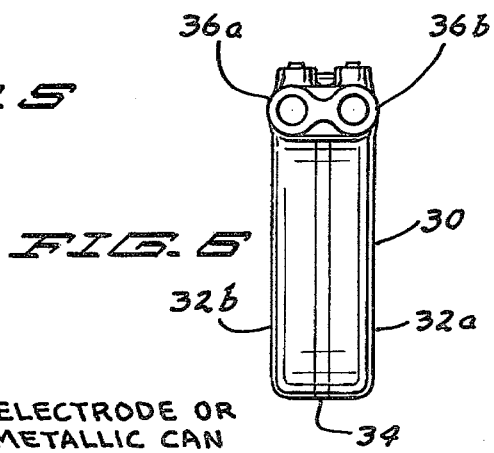
FIG. 6 illustrates a third embodiment of the present invention.

FIG. 6, which illustrates a third embodiment of a passive sensing reference electrode 30 of the present invention, shows an implantable pulse generator metallic can 32a and 32b having insulation member 34 of ceramic or like material welded therebetween where either one of the sections 32a or 32b is designated as the passive sensing reference electrode 30, while the other half may be used as the indifferent electrode for stimulation as required. The connector sleeves 36a and 36b are clearly illustrated as previously described in FIGS. 2-5. The one section of the metallic can connects to an input of the sense amplifier.

PREFERRED MODE OF OPERATION

Figure 7:
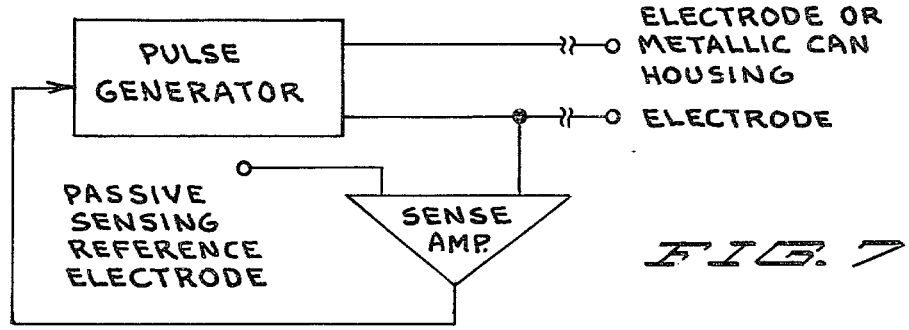
FIG. 7 illustrates an electrical circuit schematic diagram showing the passive sensing reference electrode connected to a pulse generator circuit of an implantable pulse generator.

The passive sensing reference electrodes of the first through third embodiments 10, 20 and 30 of FIGS. 2-4, 5 and 6 respectively, connect to one input terminal of a sensing amplifier of the implantable pulse generator as illustrated in the electrical circuit schematic diagram of FIG. 7. The electrical circuit block schematic diagram of FIG. 7 shows the other input terminal of the sensing amplifier connected to one of the output terminals of the implantable pulse generator or to one of the electrodes. The figure illustrates an electrical connection between the one input terminal of the sense amplifier and the passive sensing reference electrode, whether the passive sensing reference electrode is located on the connector block, positioned on the metallic can, or is half of the metallic can. The pulse generator and sensing amplifier along with other related circuit components comprises the implantable pulse generator, all of which are mounted in the enclosed and hermetically sealed metallic can of the implantable pulse generator. A pacing lead or leads connect the implantable pulse generator circuitry to the remote electrode, electrodes, or stimulating reference electrodes dependent upon whether the mode of operation is unipolar or bipolar. The dashed line in FIG. 7 illustrates that the implantable pulse generator circuitry is to the left of the dashed line and retained within the hermetically sealed metallic housing, and that the pacing lead or leads and connected remote electrode or electrodes are to the right of the dashed line.

The passive sensing reference electrode may position on or adjacent to the metallic can of the implantable pulse generator and connects internally to one input of the sensing amplifier as illustrated in FIG. 7. The sensing amplifier of FIG. 7 senses pacing with capture determination where the effect of the stimulation has to be evaluated immediately by connecting the passive sensing reference electrode directly to the sense amplifier thereby reducing stimulation afterpotentials and minimizing electrical disturbance of the sense amplifier.

For dual chamber pacing where ventricular sensing has to remain intact as much as possible during atrial stimulus in order to detect spontaneous ventricular activity, the passive sensing reference electrode or electrodes may connect directly to both a ventricular sensing amplifier and an atrial sensing amplifier.

The passive sensing reference electrodes are positioned on the implantable pulse generator metallic can in FIGS. 2-4, 5 and 6 as illustrated in such a way that electrical continuity with the tissue or body fluid is assured. The determination is made by medical personnel as to the best positioning of the passive sensing reference electrode, whether the passive sensing reference electrode is located on the connector block as in FIGS. 2-4, on the metallic can itself as in FIG. 5, or as an inherent part of the metallic can as in FIG. 6.

Various modifications can be made to the passive sensing reference electrode of the present invention without departing from the apparent scope of the present invention. Inherently, more than one passive sensing reference electrode may be provided on or adjacent to the metallic can, and may be positioned as deemed necessary for best sensing. The passive sensing reference electrode or electrodes may be connected to one or more sense amplifiers as predetermined.

Having thus described the invention, there is claimed as new and desired to be secured by Letters Patent:

1. In an implantable pulse generator having a terminal from which said implantable pulse generator both senses electrical activity and electrically stimulates body tissue via a single remotely attached electrode having a first surface area and wherein a first reference electrode is used for said stimulating, the improvement comprising:
   a second reference electrode electrically isolated from said first reference electrode fixedly attached to said implantable pulse generator used as a reference electrode for said sensing.

2. The improvement according to claim 1 wherein said second reference electrode is fixedly attached to said output terminal.

3. The improvement according to claim 1 wherein said second reference electrode is located upon the surface of said implantable pulse generator.

4. The improvement according to claim 1 or claim 2 or claim 3 wherein said second reference electrode has a second surface area approximately equal to that of said first surface area.

5. A body implantable apparatus for stimulating body tissue comprising:
   an electrode for contacting said body tissue;

a pulse generator electrically coupled to said electrode having means for evaluating signals sensed by said electrode and means for generating stimulating pulses for transferring to said electrode in response thereto;

a first reference electrode coupled to said generating means; and a second reference electrode fixedly attached to said pulse generator coupled to said evaluating means.

6. Body implantable apparatus according to claim 9 wherein said pulse generator means further comprises an output terminal coupled to said electrode, said evaluating means, and said generating means and said second reference electrode is fixedly attached to said output terminal.

* * * * *

UNITED STATES PATENT AND TRADEMARK OFFICE
CERTIFICATE OF CORRECTION

PATENT NO. : 4,310,000
DATED : January 12, 1982
INVENTOR(S) : Fredric W. Lindemans It is certified that error appears in the above-identified patent and that said Letters Patent is hereby corrected as shown below:

Column 6, line 3, "9" should read -- 5 --.

Signed and Sealed this

Thirty-first Day of August 1982

[SEAL]

Attest:

GERALD J. MOSSINGHOFF

*Attesting Officer*  *Commissioner of Patents and Trademarks*